United States Patent
Moran

(10) Patent No.: US 7,117,814 B2
(45) Date of Patent: *Oct. 10, 2006

(54) METHOD OF PRODUCING AVIAN EGGS AND BIRDS OF GERM-FREE STATUS

(75) Inventor: Leonard Moran, Ballina (IE)

(73) Assignee: Ovagen International Limited, County Mayo (IE)

( * ) Notice: Subject to any disclaimer, the term of this patent is extended or adjusted under 35 U.S.C. 154(b) by 143 days.

This patent is subject to a terminal disclaimer.

(21) Appl. No.: 10/788,338

(22) Filed: Mar. 1, 2004

(65) Prior Publication Data

US 2004/0200420 A1 Oct. 14, 2004

Related U.S. Application Data

(63) Continuation-in-part of application No. 10/255,097, filed on Sep. 26, 2002, now Pat. No. 6,718,909.

(30) Foreign Application Priority Data

Sep. 26, 2001 (EP) ................... 01650109

(51) Int. Cl.
*A01K 45/00* (2006.01)

(52) U.S. Cl. .................................... 119/6.8

(58) Field of Classification Search ............... 119/6.8, 119/174, 300, 311, 417, 418, 419
See application file for complete search history.

(56) References Cited

U.S. PATENT DOCUMENTS

| | | | |
|---|---|---|---|
| 2,887,090 A * | 5/1959 | William | 119/6.8 |
| 4,381,732 A | 5/1983 | Huisinga | 119/45 |
| 4,511,589 A | 4/1985 | Padly et al. | 426/521 |
| 4,928,628 A | 5/1990 | Gassman et al. | 119/1 |
| 5,011,780 A | 4/1991 | Perry | 435/317 |
| 5,158,038 A | 10/1992 | Sheeks et al. | 119/6 |
| 5,206,015 A * | 4/1993 | Cox et al. | 424/93.3 |
| 5,286,641 A | 2/1994 | Naito | 435/240 |
| 5,458,875 A * | 10/1995 | Casas-Perez et al. | 424/93.45 |
| 5,575,237 A * | 11/1996 | Ferguson | 119/6.8 |
| 5,698,193 A | 12/1997 | Kogut et al. | 424/85 |
| 5,722,342 A * | 3/1998 | Line et al. | 119/6.8 |
| 5,817,320 A * | 10/1998 | Stone | 424/278.1 |
| 5,916,869 A * | 6/1999 | Croom et al. | 514/2 |
| 5,944,652 A * | 8/1999 | Miller et al. | 600/33 |
| 5,965,087 A * | 10/1999 | Caracciolo, Jr. | 422/28 |
| 6,395,961 B1* | 5/2002 | Petitte et al. | 800/21 |
| 6,491,910 B1* | 12/2002 | Schneitz et al. | 424/93.3 |
| 6,573,097 B1* | 6/2003 | Cantrell et al. | 435/349 |
| 6,718,909 B1* | 4/2004 | Moran | 119/6.8 |
| 2003/0106082 A1* | 6/2003 | Schatten et al. | 800/14 |

FOREIGN PATENT DOCUMENTS

| | | | |
|---|---|---|---|
| EP | 0295964 A1 | | 12/1988 |
| EP | 0511431 A2 | | 11/1992 |
| GB | 2229440 | * | 9/1990 |

* cited by examiner

*Primary Examiner*—Peter M. Poon
*Assistant Examiner*—David Parsley
(74) *Attorney, Agent, or Firm*—Jacobson Holman PLLC

(57) ABSTRACT

A method of rearing a bird of germ-free status comprises housing a bird as a parent bird, surgically removing an egg in its shell from the parent bird prior to transfer of the egg to the cloaca in the parent bird, incubating the egg still in its shell and hatching the egg to produce a laying bird. The production of avian eggs of germ-free status is also provided.

24 Claims, No Drawings

METHOD OF PRODUCING AVIAN EGGS AND BIRDS OF GERM-FREE STATUS

This is a Continuation-in-part of application Ser. No. 10/255,097 filed Sep. 26, 2002 now U.S. Pat. No. 6,718,909.

FIELD OF THE INVENTION

The present invention relates to a method of rearing a bird of germ-free status. It further relates to the production of avian eggs of germ-free status. It also relates to a method of producing various eggs and birds.

In this specification, the term "germ-free" is used very broadly and relates to many pathogens and infections that can be carried by birds, particularly, poultry such as chickens and turkeys which are used widely to produce flocks of birds for breeding to produce fertile eggs for commercial production and to produce eggs and meat for human consumption. Further, such eggs and birds are used in the manufacture of a wide range of biological substances including vaccines, fibroblasts and proteins, both for therapeutic and prophylactic use in people and animals. Poultry, particularly hens, is used extensively for these tasks. They are further used extensively for diagnostic tests and the production of transgenic eggs and birds. Many of these uses require eggs and/or the birds produced from them to be free of all contaminants such as infections, including a variety of species of parasite, bacteria, mycoplasma, viruses, retroviruses, prions, DNA and RNA fragments. Sometimes, the viruses can be small viruses including picoma and parvo viruses. Some of the bacteria from which eggs are often contaminated include Clostridia and Enterobacteria. There are many non-pathogenic organisms that should be controlled. Similarly, many of the micro-organisms which include parasites, aerobic and anaerobic bacteria, commensal species and species associated with the gut, are undesirable. Similarly, mycoplasma, viruses including retroviruses, prions, fungi, yeast and moulds are also undesirable.

Therefore, the term "germ-free status" includes all of these and is much broader than just free of specified pathogens. For example, conventional specific pathogen free (SPF) are not specified free from some viruses and indeed can be contaminated with bacteria and indeed for certain uses, these may be sufficient. The use to which the eggs and the birds are to be put will determine the contaminants that the egg or bird must be free of. Conventional contaminant free and some SPF eggs are derived by treating fresh naturally laid eggs with chemicals, including disinfectants and antibiotics, and placing them in isolators. Such naturally laid eggs are taken from selected parent stock birds. While these methods have been relatively successful in the production of SPF eggs, they have not been truly successful in producing what are germ-free eggs as the chemicals are not able to eliminate contamination from, for example, bacteria entering the pores of the eggshell immediately after laying and before disinfection. Contamination of eggs results in loss of compliance with specifications and, in many instances, loss of commercial value and utility.

Additionally, the term "similar" is used in a broad sense and could refer to the same species or indeed, could be not the same species that had been reared together naturally for some considerable time, or might not, for example, be the same species but might have some other similarity that was required. Thus, they might not be of a particular species but might have effectively been grown naturally over many years to form a flock that could be described as similar.

DESCRIPTION OF PRIOR ART

U.S. Pat. No. 5,011,780 (Margaret Mary Perry) describes an in vitro avian embryo culture technique which, while not particularly applicable to the present invention, describes in some detail the embryonic development of eggs. This specification is directed to the incubation of an embryo in a closed container after the embryo has been removed from its shell. Indeed, in this specification, the container used is preferably part of an egg shell which has been chosen from the same species as is being cultured or, in the terms of the present invention, from a similar hen. This invention is directed towards the genetic engineering of poultry but also to the investigation of fundamental mechanisms of avian development. It is directed towards providing an alternative to surgical intervention in the laying hen.

Similarly, U.S. Pat. No. 5,286,641 (Naito et al) discloses an in vitro culture method for a fertilized ovum of a hen in which an embryo which has just been fertilized is taken from an upper portion of the magnum of the oviduct of a hen within an hour or so after oviposition and then subsequently cultured. However, both of these specifications merely disclose the artificial culturing of eggs and do not deal with the purpose of the present invention.

OBJECTS OF THE INVENTION

The present invention is directed towards providing eggs of germ-free status to allow various diagnostic tests to be performed. Further, the invention is directed towards providing eggs and birds that could be used in the manufacture of a wide range of biological substances. Thus, the invention is directed towards providing both eggs and birds which are free of all contaminants such as infections, including a variety of species of parasites, bacteria, mycoplasma, viruses, retroviruses, prions, DNA and RNA fragments.

Indeed, it is an object of the present invention to produce, what are effectively sterile eggs and hens which could be used as food, in certain specified situations for particularly delicate patients.

SUMMARY OF INVENTION

The invention provides a method of rearing a bird of germ-free status. The method comprises choosing a bird and housing it as a parent bird and then removing the egg from the parent bird prior to the transfer of the egg to the cloaca in the parent bird, thus avoiding most contaminants to the egg that would normally occur within the parent bird. As an eggshell is porous external contamination is a major problem. Then, the egg is incubated in a sterile environment and hatched to produce a laying bird. Generally speaking, these laying birds will all come from the one flock of similar birds, all reared under the same conditions. They may, for example, be hatched naturally in a sterile environment. The flock may already be a flock of birds which are of a particular contaminant free status which may have been produced, for example, by natural selection under controlled conditions. The whole purpose is to provide germ-free birds. Very often, therefore, samples of the laying birds will be removed and tested for specific contaminants to provide a measure of the germ-free status. By an iterative process, it will be possible to eventually produce a flock of birds which will be virtually sterile and of a germ-free status. Thus, initially, when the laying birds are produced, they will not form a flock of sufficiently germ-free status and it will be necessary to continue the process until birds of the desired germ-free status are obtained.

In accordance with the invention, the egg is surgically removed from the parent bird by aseptic surgical laparotomy. Thus, the birds are euthanased and then the surgical operation is performed.

The surgical operation, in one method according to the invention, comprises:
performing a laparotomy incision and tying off the oviduct of the bird at both ends with sutures;
transecting the oviduct distal to each suture;
removing the egg enclosed in the oviduct;
sterilising the oviduct;
removing the egg; and
sterilising the egg.

The eggs are generally removed at a time prior to and as close as possible to the transfer time when the egg would naturally transfer to the cloaca and thus the laying pattern of a parent bird will often be recorded over time to ensure that this is done as close to the estimated transfer time as possible.

Indeed, the sterility can be further improved by feeding the laying birds, in the sterile environment, with food containing normal gutflora or sterile food. It will be appreciated that when birds are hatched which are not laying birds, they will then be retained for subsequent fertilisation of the laying birds. In this way, the whole flock can be sterile.

It will be possible, in the present invention, to produce simply the eggs for subsequent use. When eggs are required of a germ-free status, the first thing to do is to incubate the eggs by using the desired parent birds. Then, when the parent birds have been tested for specified contaminants to provide a measure of the germ-free status, house that laying bird in another sterile environment and use that laying bird to lay eggs which will have a germ-free status.

Preferably, on laying, the outer shell of the egg is sterilised.

As stated above not all of the steps of the method have to be performed in a sterile environment. It is necessary that the step of removing the egg from the parent bird prior to the transfer of the egg to the cloaca in the parent bird is performed in a sterile environment. The advantage of this is that the egg is not contaminated during removal of the egg. Additionally after removing the egg from the parent bird in a sterile environment the steps of incubating the egg in its shell, hatching the egg to produce a laying bird, housing the laying bird and using the laying bird to lay the egg should also be carried out in a sterile environment to retain the sterility of the egg produced from the parent bird, the laying bird hatched from that egg and the egg produced from the laying bird. The steps carried out prior to removal of the egg from the parent bird such as housing a bird or obtaining a flock of birds may be carried out in a sterile or non-sterile environment.

DETAILED DESCRIPTION OF THE INVENTION

The invention will be more clearly understood from the following description of the method according to the present invention.

Essentially, what the present invention does is to provide the use of artificially derived eggs from parent birds in the production of eggs and derived birds to give laying birds for the control of micro-organisms. The said eggs and birds are as appropriate to their utility subsequently hatched, reared, maintained and bred, either conventionally, or in some form of isolator or sterile environment.

METHOD

Fifty adult female and five adult male chickens of known SPF status were maintained on selected diets and allowed to breed naturally. Timing of egg laying (oviposition) was recorded individually for each female over a two-week period. The mean time of day (time, L) when an egg was laid was calculated for each female. The time of day for L-3h was calculated and the period from L-3 to L was nominated as the derivation interval. This interval was the time in which aseptic surgical laparotomy was performed for removal of the most developed eggs in each bird.

For the procedure, birds were euthanased by cervical dislocation and shortly afterwards prepared. Birds were submerged in a disinfectant solution for 5 minutes. Feathers were removed from the ventral thorax and abdomen and the exposed skin sterilised using a 50% solution of iodine in alcohol heated to 37° C. Each bird was then placed under a specially adapted surgical isolator sterilised with a 5% solution of peracetic acid and containing sterile instruments and a 500 ml flask containing iodine in alcohol. The bird was covered with a sterile drape and a sterile entry port of the isolator was then placed over the drape. A laparotomy incision was made and the oviduct (typically the uterus) was tied off at both sides of the egg using suture material. The oviduct was then transected distal to each of the sutures from the egg and the oviduct containing the egg was removed from the females' abdomen. The uterus-enclosed egg was then placed in the iodine/alcohol solution for five minutes after which the oviduct-enclosed egg was transferred via an entry port from the surgical isolator to a receiving isolator. In the receiving isolator, the oviduct was incised, the egg removed, swabbed with a disinfectant solution and transferred to an isolator adapted as a hatchery incubator.

Within one day of hatching, live chickens were removed from the hatchery isolator and transferred to two large-scale rearing isolators suitable for rearing groups of young chickens. Chickens were reared on commercial diets sterilised by radiation. At 18 days of age, five chickens were removed from each of the rearing isolators, euthanased and sampled for bacteriology by aerobic and anaerobic culture. Samples included liver, spleen, heart blood, vagina/cloaca, caecal and small intestinal digesta and faeces.

RESULTS

Viable chickens were hatched successfully from the artificially derived eggs (hatchability>50% more often>90%). No anaerobic or aerobic bacteria were isolated from the chickens sampled.

CONCLUSION

A safe and highly effective method for artificial production of germ-free fertile eggs in chickens was established. Eggs were viable and produced viable germ-free chickens which were successfully maintained in isolators.

It will be appreciated that according to the invention, essentially these are artificially or surgically derived eggs which, strictly speaking, in accordance with the present invention means that the egg is removed from the parent bird prior to the transfer of the egg to an area of potential contamination. Ideally, one raises the bird as a parent bird in a sterile environment, feeding the bird with sterile food.

Then, the egg is removed from the parent bird artificially prior to the transfer of the egg to an area of potential contamination in the parent bird and then the egg is incubated and hatched to produce a laying bird which is kept in this sterile environment.

Female parent birds may be either live or recently killed. Live birds may, as consistent with ethical, legal and animal welfare considerations, be fully conscious, sedated or anaesthetised. Eggs and ova may be either fertilized or unfertilized.

Infectious organisms that may be controlled by the invention include organisms that can be pathogenic or non-pathogenic to the relevant species. These include avian species (typically chickens, fowls and turkeys), humans and other mammals (typically dogs, cats, horses, cattle, pigs, sheep, goats, rats and mice). For the purposes of the invention, micro-organisms include parasites, bacteria (including anaerobic and aerobic species, commensal species and species associated with the gut), mycoplasma, viruses (including retroviruses), prions, fungi, yeasts, moulds and DNA and RNA fragments.

If fertile eggs are used to produce offspring or derived birds, then the eggs may be hatched, reared, maintained and bred in either conventional husbandry systems, germ-free systems or in isolators to control the entry of micro-organisms.

According to the invention, for maximum freedom from micro-organisms eggs should preferably be derived aseptically from parent females (unless they are also germ-free) and the life-cycle should be completed in isolators. The life-cycle may be completed outside isolators when germ-free eggs and birds are produced.

According to the present invention, the aseptic derivation of eggs and, if appropriate hatching, rearing, maintenance and breeding of birds may be used in combination with another method of controlling microbial contamination. Such methods include disinfectants, antimicrobials, antibiotics, antiviral agents, antiparasitics, immunomodulators and vaccines.

It will be appreciated that in certain circumstances, when taking selected birds as parent birds, the laying birds produced may not in fact be sufficiently free of contaminants to produce laying birds of the right quality. It may then be necessary to carry out the same steps again using the eggs produced from such laying birds and artificially removing the eggs from these laying birds to provide further laying birds which hopefully will be germ-free.

While in the above, the description has related entirely to poultry and specifically hens, it will be appreciated that the present invention may be carried out on other birds.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiment and methods described above, but may be varied within the scope of the claims.

The invention claimed is:

1. A method of providing an egg of a specified germ-free status in a sterile environment comprising the steps of:
   (a) providing a bird of germ-free status comprising the steps of:
      housing a bird as a parent bird;
      removing an egg in its shell from the parent bird prior to transfer of the egg to the cloaca in the parent bird; and
      incubating the egg in its shell and hatching the egg to produce a laying bird;
   (b) housing the laying bird;
   (c) using the laying bird to lay another egg; and
   (d) removing the egg obtained from step (c) to another sterile environment.

2. The method according to claim 1, in which the egg is, on laying, immediately removed and the shell of the egg is sterilized.

3. A method of providing an egg of a germ-free status in a sterile environment comprising the steps of:
   (a) providing a bird of germ-free status comprising the steps of:
      obtaining a flock of similar birds all reared under the same conditions;
      housing one of the birds as a parent bird;
      removing an egg from the parent bird prior to transfer of the egg to the cloaca in the parent bird; and
      incubating the egg in its shell and hatching the egg to produce a laying bird;
   (b) housing the laying bird;
   (c) using the laying bird to lay another egg; and
   (d) removing the egg obtained from step (c) to another sterile environment.

4. The method according to claim 3, in which the egg is, on laying, immediately removed and the shell of the egg is sterilized.

5. A method of providing an egg of a germ-free status in a sterile environment comprising the steps of:
   (a) providing a bird of germ-free status comprising the steps of:
      obtaining a flock of similar birds all reared under the same conditions;
      housing one of the birds as a parent bird;
      performing a laparotomy incision and tying off the oviduct of the bird at both ends with sutures prior to transfer of the egg to the cloaca in the parent bird;
      transecting the oviduct distal to each suture;
      removing the egg in its shell enclosed in the oviduct;
      sterilizing the oviduct;
      removing the egg;
      sterilizing the exterior of the egg shell; and
      incubating the egg and hatching the egg to produce a laying bird;
   (b) housing the laying bird;
   (c) using the laying bird to lay another egg; and
   (d) removing the egg obtained from step (c) to another sterile environment.

6. The method according to claim 5, in which the egg is, on laying, immediately removed and the shell of the egg is sterlized.

7. A method of providing an egg of a germ-free status comprising the steps of, in a sterile environment:
   housing a bird as a parent bird;
   removing an egg in its shell from the parent bird prior to transfer of the egg to the cloaca in the parent bird;
   incubating the egg in its shell and hatching the egg to produce a laying bird;
   testing the laying bird for specific contaminants to provide a measure of the germ-free status;
   housing the laying bird in another sterile environment;
   using the laying bird to lay the egg of a germ-free status; and
   removing the egg of a germ-free status to another sterile environment.

8. The method according to claim 7, in which the parent bird is chosen from a flock of similar birds, all reared under the same conditions and the laying bird produced is used to form a flock of birds of germ-free status.

9. The method according to claim 7, in which laying bird forms part of a flock and after the laying birds are hatched, a sample of the laying birds is removed and tested for specific contaminants to provide a measure of the germ-free status of the flock.

10. The method according to claim 7, in which the laying bird forms part of a flock and after the laying birds are hatched, a sample of the laying birds is removed and tested for specific contaminants to provide a measure of the germ-free status of the flock and in which when the germ-free status is not achieved in the laying bird, the laying bird is used as a parent bird in the method.

11. The method according to claim 7, in which the egg is surgically removed from the parent bird and comprises the steps of:
   performing a laparotomy incision and tying off the oviduct of the bird at both ends with sutures;
   transecting the oviduct distal to each suture;
   removing the egg enclosed in the oviduct;
   sterlizing the oviduct;
   removing the egg; and
   sterlizing the egg.

12. The method according to claim 7, in which the egg of germ-free status is, on laying, immediately removed and the shell of the egg of a germ-free status is sterlized.

13. A method of providing an egg of a specified germ-free status comprising the steps of:
   (a) providing a bird of germ-free status comprising the steps of:
      housing a bird as a parent bird;
      in a sterile environment removing an egg in its shell from the parent bird prior to transfer of the egg to the cloaca in the parent bird; and
      in a sterile environment incubating the egg in its shell and hatching the egg to produce a laying bird;
   (b) housing the laying bird in a sterile environment; and
   (c) using the laying bird to lay the egg of a specified germ-free status in a sterile environment.

14. The method according to claim 13, in which the egg of a specified germ-free status is, on laying, immediately removed and the shell of the egg of a specified germ-free status is sterilized.

15. A method of providing an egg of a germ-free status comprising the steps of:
   (a) providing a bird of germ-free status comprising obtaining a flock of similar birds all reared under the same conditions;
      housing one of the birds as a parent bird; and
      in a sterile environment removing an egg in its shell from the parent bird prior to transfer of the egg to the cloaca in the parent bird;
      in a sterile environment incubating the egg in its shell and hatching the egg to produce a laying bird;
   (b) housing the laying bird in a sterile environment; and
   (c) using the laying bird to lay the egg of a germ-free status in a sterile environment.

16. The method according to claim 15, in which the egg of a germ-free status is, on laying, immediately removed and the shell of the, egg of a germ-free status is sterilized.

17. A method of providing an egg of a germ-free status comprising the steps of:
   (a) providing a bird of germ-free status comprising the steps of:
      obtaining a flock of similar birds all reared under the same conditions;
      housing one of the birds as a parent bird;
      in a sterile environment performing a laparotomy incision and tying off the oviduct of the bird at both ends with sutures prior to transfer of an egg to the cloaca in the parent bird;
      transecting the oviduct distal to each suture in a sterile environment;
      removing the egg in its shell enclosed in the oviduct in a sterile environment;
      sterilizing the oviduct;
      removing the egg in a sterile environment; and
      sterilizing the exterior of the egg shell;
   (b) incubating the egg and hatching the egg to produce a laying bird in a sterile environment;
   (c) housing the laying bird in a sterile environment; and
   (d) using the laying bird to lay the egg of a germ-free status in a sterile environment.

18. The method according to claim 17, in which the egg of a germ-free status is, on laying, immediately removed and the shell of the egg of a germ-free status is sterilized.

19. A method of providing an egg of a germ-free status comprising the steps of:
   housing a bird as a parent bird;
   in a sterile environment removing an egg in its shell from the parent bird prior to transfer of the egg to the cloaca in the parent bird;
   incubating the egg in its shell and hatching the egg to produce a laying bird in a sterile environment;
   testing the laying bird for specific contaminants to provide a measure of the germ-free status;
   housing the laying bird in a sterile environment;
   using the laying bird to lay the egg of a germ-free status in a sterile environment; and
   removing the egg of a germ-free status to another sterile environment.

20. The method according to claim 19, in which the parent bird is chosen from a flock of similar birds, all reared under the same conditions and the laying bird produced is used to form a flock of birds of germ-free status.

21. The method according to claim 19, in which laying bird forms part of a flock and after the laying birds are hatched, a sample of the laying birds is removed and tested for specific contaminants to provide a measure of the germ-free status of the flock.

22. The method according to claim 19, in which the laying bird forms part of a flock and after the laying birds are hatched, a sample of the laying birds is removed and tested for specific contaminants to provide a measure of the germ-free status of the flock and in which when the germ-free status is not achieved in the laying bird, the laying bird is used as a parent bird in the method.

23. The method according to claim 19, in which the egg is surgically removed from the parent bird and comprises the steps of:
   performing a laparotomy incision and tying off the oviduct of the bird at both ends with sutures;
   transecting the oviduct distal to each suture;
   removing the egg enclosed in the oviduct;
   sterilizing the oviduct;
   removing the egg; and
   sterilizing the egg.

24. The method according to claim 19, in which the egg is, on laying, immediately removed and the shell of the egg is sterilized.

* * * * *